United States Patent [19]

Fukuda et al.

[11] 4,282,328

[45] Aug. 4, 1981

[54] APPARATUS FOR CULTIVATING AEROBIC MICROORGANISMS AND PROCESS FOR CULTIVATION USING THE SAME

[75] Inventors: Hideki Fukuda, Hyogo; Takeshi Shiotani, Takasago; Wataru Okada, Kobe, all of Japan

[73] Assignee: Kanegafuchi Kagaku Kogyo Kabushiki Kaisha, Osaka, Japan

[21] Appl. No.: 105,417

[22] Filed: Dec. 19, 1979

[51] Int. Cl.³ .............................................. C12N 1/16
[52] U.S. Cl. ..................................... 435/255; 261/76; 261/DIG. 75; 435/314; 435/813; 435/818
[58] Field of Search ............... 435/255, 314, 243, 248, 435/249, 250, 253, 254, 313, 813, 818; 261/DIG. 75, 76

[56] References Cited

U.S. PATENT DOCUMENTS

| 2,750,328 | 6/1956 | Stimpson et al. | 435/314 |
| 2,983,652 | 5/1961 | Baerfuss | 435/314 |
| 3,824,151 | 7/1974 | Iijima et al. | 435/314 X |
| 3,957,585 | 5/1976 | Malick | 435/314 X |
| 3,985,622 | 10/1976 | Hawkins | 435/314 X |
| 3,986,934 | 10/1976 | Müller | 435/314 |

FOREIGN PATENT DOCUMENTS 20552 7/1970 Japan .
24666 8/1957 United Kingdom .

Primary Examiner—Robert J. Warden
Attorney, Agent, or Firm—Moonray Kojima

[57] ABSTRACT

Apparatus for cultivating aerobic microorganisms is provided which comprises cell multiplying compartment and cell ripening compartment. The invention also provides a cultivation process using the same apparatus. The invention improves oxygen transfer rate and utilization of oxygen, thus enabling cultivation at a higher concentration of microorganisms as compared with any conventional process.

11 Claims, 4 Drawing Figures

APPARATUS FOR CULTIVATING AEROBIC MICROORGANISMS AND PROCESS FOR CULTIVATION USING THE SAME

DETAILED DESCRIPTION OF THE INVENTION

The present invention is directed to an aerobic cultivation apparatus of aerobic microorganisms and to a cultivation process using the same.

In the fermentation industry, there has been known batch or continuous cultivation processes of microorganisms, and the former has been employed more frequently than the latter. Batch processes, nevertheless, have disadvantages that in nongrowth-associated type cultivation where growth of microorganisms is not proportional to production of fermented products, which is accompanied with cultivation and ripeness (operation by supplying such an amount of main carbon sources and nutrients—hereinafter referred to as "nutrients"—as required in maintenance and metabolism of microorganisms), the amount of nutrients supplied has to be controlled batch by batch, which control is difficult to be carried out perfectly, thereby causing irregularity of the product.

On the other hand, in continuous operation inside of a reactor can be maintained at steady state, and thus change with the lapse of time rarely takes place, thereby a uniform quality of products being obtained. Accordingly, there is a great need for a cultivation process conducting multiplication and ripeness continuously.

In the Japanese Patent Publication (examined) No. 11291/1961, a process is disclosed using a continuous fermentor of tanks-in series type. The Japanese Patent Publication (examined) No. 20552/1970 proposes a process for using a continuous fermentor of multistage tower type which is improved from tanks-in series type to air-bubble tower type.

In the cultivation of aerobic microorganisms, notwithstanding, utmost amount of oxygen is required at a period of exponential multiplication and thus multiplication is often suppressed owing to shortage of oxygen supplied even in the presence of a sufficient amount of nutrients. Hence, efficiency of a fermentor of aerobic microorganisms is decided upon by the value of oxygen transfer rate. When fermentors disclosed in the Japanese Patent Publication (examined) Nos. 11291/1961 and 20552/1970 are observed in respect of oxygen transfer rate, both fermentors have almost the same value in the fermentor (or each unit room). For the reason, shortage of oxygen happens in the fermentor (or in the unit room) which corresponds to a period of exponential multiplication, adversely, oxygen is superfluous in the fermentor (or each unit room) corresponding to ripening compartment. This uneffective utilization of oxygen sets a limit to the cell concentration.

An object of the present invention is to provide a cultivation apparatus and a process of aerobic microorganisms which improve oxygen transfer rate and efficiency of oxygen utilization.

Another object of the present invention is to provide a cultivation apparatus and a process of aerobic microorganisms which enable cultivation at a higher cell concentration as compared with a conventional apparatus and process.

It has now been discovered by the present inventors through a series of study that foregoing objects can be accomplished by a fermentor having two functions, i.e. a fermentor comprised of cell multiplying compartment (I) and cell ripening compartment (II).

The principal function of the cell multiplying compartment (I) is to cultivate and multiply cells and that of the cell ripening compartment (II) is to change the interior activities of cells, to allow the cells produce the fermented products, to uniformalize the distribution of cell age, and the like. In order to sufficiently expect and enjoy such functions as aforesaid as well as higher and effective effects in oxygen transfer rate and utilization of oxygen, each compartment comprising the following structure has been found productive of the desired effects most satisfactorily:

Cell multiplying compartment (I) . . . a draft tube fermentor equipped with a draft tube inside the compartment Cell ripening compartment (II) . . . a multistage perforated plates fermentor of which inside is partitioned with one or more, preferably up to 10 perforated plates.

By connecting the cell ripening compartment (II) with the top of the cell multiplying compartment (I), constructed as above, not only is the cell concentration increased surprisingly, but also the ripening effects are achieved satisfactorily.

A feature of the present invention is to enhance oxygen transfer rate and cell concentration by effecting two functions (multiplication and ripening) in a single fermentor employed. The present apparatus achieving two different functions differs fundamentally from any known apparatus proposed in the Japanese Patent Publication Nos. 11291/1961, 20552/1970 and the like.

Figures 1, 2:
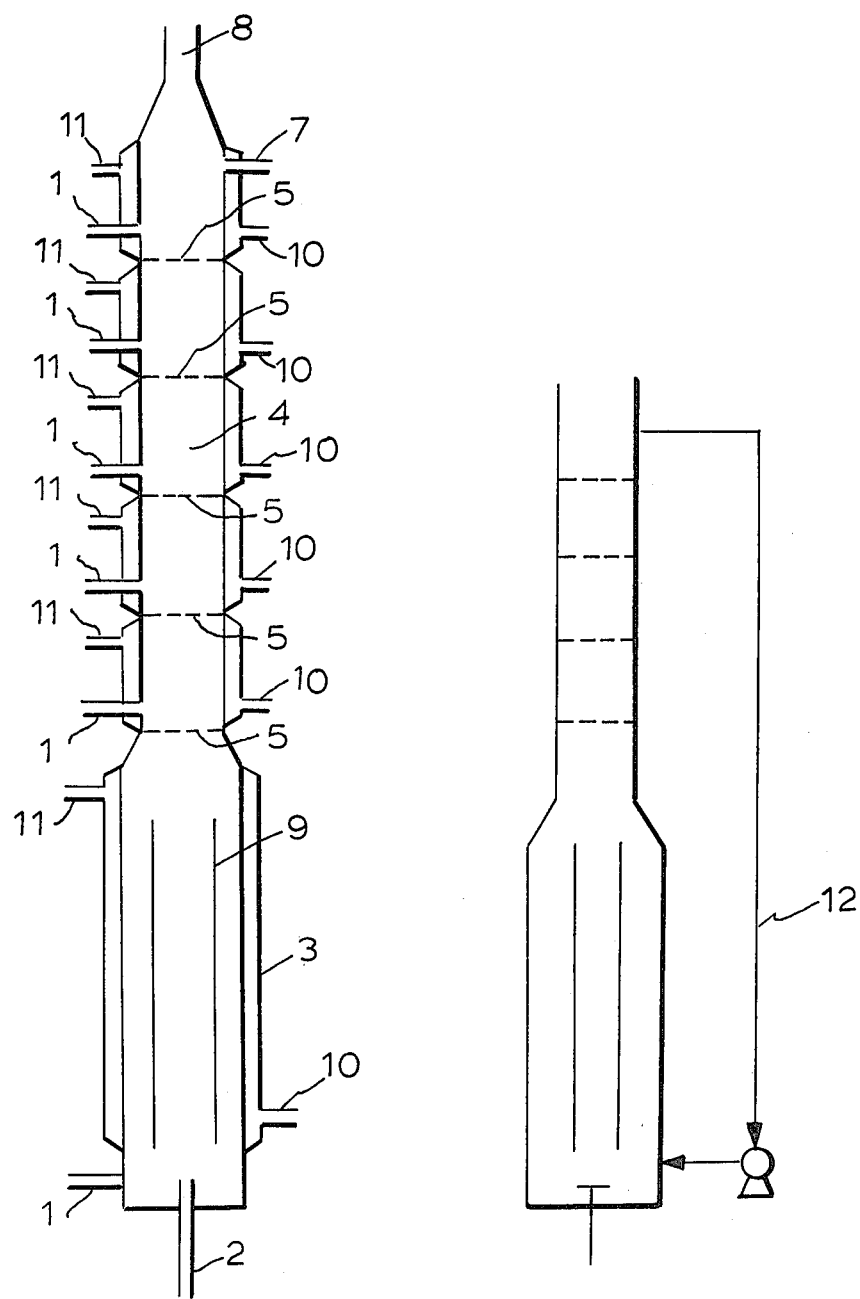
FIG. 1 shows a vertical sectional view of an apparatus of the present invention.
FIG. 2 illustrates a schematic sectional view of another apparatus of the present invention.

The apparatus of the present invention will be described with reference to FIG. 1 illustrating an embodiment.

The present apparatus is comprised of cell multiplying compartment (I) and cell ripening compartment (II). The numeral (1) is a nutrients supply line, (2) is an air supply line. (3) is a jacket, (9) is a draft tube, (4) is a unit room partitioned with the perforated plates, (5) is a perforated plate, (6) is a jacket, (7) is a liquor outlet and (8) is an air outlet, respectively. (10) or (11) is a cooling water inlet or an outlet. Air is fed through the air supply line (2) and sparged in the draft tube (9). Air sparged is mingled vigorously with the culture broth while ascending upwardly in the draft tube (9). When the mixed stream of sparged air and culture broth goes up, further going up of the mixed stream is interrupted by the perforated plate located at the bottom of the cell ripening compartment. Most of the mixed stream is therefore pushed away outside the draft tube, reverses its direction, then descending downwardly by dint of air lift action. Upon arriving at the bottom, the culture broth is enfolded in ascending stream, then repetition of circulation movement occurs.

In order to allow this action and movement to take place more effectively, the study has been made on the desired structure of the cell multiplying compartment and found that it is preferred to employ a draft tube fermentor in which a circular or a rectangular draft tube having a ratio of the cross sectional area of the draft tube to that of the draft tube fermentor ranging from about 0.2 to about 0.9, more preferably from about 0.4 to 0.9 is installed in the fermentor whose ratio of the height to the diameter ranges from about 1.5 to about 15, more preferably from about 3 to about 10.

Air may be supplied through the line (2) using nozzles, a sparger, a porous structure of a fused metal and the like. A highly concentrated oxygen containing air may be also employed to increase partial pressure of oxygen supplied. In the case of cultivation evolving a great amount of fermentation heat, the use of double wall draft tube into which cooling water is passed through is recommended.

As is apparent from the foregoing action, the perforated plate positioned at the bottom of the cell ripening compartment produces the following effects in relation with the cell multiplying compartment;

1. To increase a hold-up effect of the cell multiplying compartment. That is, oxygen transfer rate is raised because air resides in the cell multiplying compartment longer to increase contact area between a gas phase and a liquid phase.

2. To enhance partial pressure of oxygen by the cell multiplying compartment being pressurized, caused by prevented passage of air by the perforated plate.

Moreover, the cell multiplying compartment is further pressurized even by mounting the cell ripening compartment on the cell multiplying compartment.

The cell ripening compartment is comprised of a plurality of unit rooms partitioned by one or more perforated plates, preferably up to about 10 perforated plates. As the perforated plate, a plate having numerous perforations, a wire-netting, a metal screen or the like may be suitably employed. The size and number of perforation are decided upon according to the size of the apparatus, the kind of reaction of microorganisms desired. To give satisfactory effects to the cell multiplying compartment and to provide uniform mixing in each unit room, the diameter of a perforation is up to about 15 mm, preferably about 1 to about 10 mm, the ratio of the perforated area to the cross sectional area of the perforated plate (hereinafter referred to as perforation rate) is up to about 30%, preferably about 2 to about 20%.

The number of unit rooms are suitably determined according to the kind of fermentation desired, the height of the apparatus, the volume, the pressure loss and the like. Jacket (6) is designed for cooling but need not be used if satisfactory results are obtained with a cooling means with which the cell multiplying compartment is equipped. Air may also be fed into each of unit rooms in order to provide intimate and effective mixing or to supply the deficiency of oxygen.

The present apparatus can utilize oxygen more effectively to consequently eliminate the inhibition of growth resulting from shortage of oxygen, whereby cell concentration can be surprisingly increased.

Another feature of the present invention is to create different flows between the two compartments. In the cell multiplying compartment, an almost homogeneous and uniform flow (complete mixing as a mixing characteristic) is maintained, while in the cell ripening compartment a uniform mixing does not occur because the compartment is partitioned by the perforated plates (flow close to piston flow or plug flow as a mixing characteristic). By so particularly devising, the following effects are produced:

1. To attain the purpose of multiplying cells, it is desired to maintain the cells in logarithmic growth phase. During the phase, increased cell concentration accelerates the growth rate. Accordingly, when cultivation is carried out at an enhanced cell concentration under the conditions where nutrients are uniformly supplied to the entire compartment, a superior productivity of cells is obtained. On the other hand, should the cell multiplying compartment be partitioned as well, the cell concentration varies at every unit room. Thus, in a unit room where the cell concentration is low, the multiplication rate decreases, thereby leading to the decrease in productivity of cells. For these reasons, the cell multiplying compartment, constructed to provide complete mixing is preferred.

2. Ripeness is mainly to lower growth rate or to uniformalize the cell age. Thus, the smaller the range of residence time distribution of cells becomes, the better. For the reasons, a piston flow or plug flow is desired to take place in the cell ripening compartment (if a complete mixing happens, the range of residence time distribution becomes the greatest).

For the foregoing reasons, cell productivity and ripeness efficiency as well as cell concentration can be drastically increased by the fermentor comprised of two compartments wherein different flows take place and function in one way or another.

Accordingly, the apparatus of the present invetion is especially suitable for the following cultivation:

1. Fermentation requiring a great amount of oxygen
2. Fermentation of non-growth-associated type, fermentation accompanied with ripeness
3. Cultivation requiring a fermentor having large capacity.

Furthermore, the present apparatus may be applied to the fermentation of growth-associated type wherein the growth of cells is proportioned to the fermented products. It may also be used for batch cultivation when a recycle line (12) heading from the top of the cell ripening compartment to the bottom of the cell multiplying compartment is installed, as shown in FIG. 2, and if, during the circulation, the broth is recycled to the apparatus after being supplied with nutrients and aerated.

The present apparatus is in wide and useful use, regardless of operation type (batch or continuous), fermentation type (growth-associated type or non-growth-associated type), products (cells or fermented products) and the like. By using the present apparatus the cell concentration is raised to result in increase in productivity per a unit volume, thus, only a small site is sufficient for installation thereof. The control of operation is also feasible with ease in the present apparatus. A two-line or more system as well as one-line system is of course available.

The present apparatus is suitably applied to the treatment of waste water, since it possesses a high oxygen transfer rate. In the case of treatment of waste water, operation can be effected at such a higher concentration of filth than conventional processes that the present apparatus is suitable, in particular, for the treatment of highly concentrated filth containing waste water.

It is also an advantage of the present apparatus to enable control of a degree of ripeness by the adjustment of the amount of nutrients supplied to the cell multiplying compartment and each unit room of the cell ripening compartment.

It is to minimize the range of cell age distribution why the compartment is partitioned with the perforated plates for the purpose of changing interior activities of cells (ripeness). Furthermore, the present inventors have ascertained that it is also necessary to gradually reduce the multiplication rate in order to achieve the object of ripening. For this purpose, it has been assured that the concentration of nutrients in each unit room and the amount of nutrients supplied to each unit room have to be controlled and that control is readily effected by furnishing a nutrients supply inlet with every unit room. By so doing, the ripening was stably carried out. Division of the nutrients supply inlet is particularly advantageous to the cultivation where excess supply of nutrients may cause disturbance of growth. That is, in such a cultivation system it is impossible to supply nutrients in a lump, but the present invention permits the cultivation controlling the concentration of nutrients below the range where no disturbance occurs by divided nutrients supply inlets.

The present invention will be explained in more detail by way of examples that follow.

EXAMPLE 1

Yeast strain: *Candida utilis* IAM 4215
Main carbon sources and nutrients:

| Glucose 20% | | $FeSO_4 \cdot 7H_2O$ | 50 ppm |
|---|---|---|---|
| $H_3PO_4$ | 2,500 ppm | $ZnSO_4 \cdot 7H_2O$ | 50 ppm |
| KCl | 1,200 ppm | $MnSO_4 \cdot 6H_2O$ | 10 ppm |
| $MgSO_4 \cdot 7H_2O$ | 300 ppm | $CuSO_4 \cdot 5H_2O$ | 0.5 ppm |
| Ammonium sulphate | 500 ppm | Vitamine $B_1$ | 2 ppm |

Cultivation conditions: Using a single fermentor, continuous operation is carried out at 28° C. and at pH 4.6.

Apparatus: The apparatus having the following dimensions was used in Example 1;

| Cell multiplying compartment (I); | |
|---|---|
| Diameter of the tower | 200 mm |
| Height of the tower | 800 mm |
| Diameter of the draft tube | 140 mm |
| Length of the draft tube | 500 mm |
| Cell ripening compartment (II); | |
| Diameter of the tower | 150 mm |
| Height of the tower | 1,800 mm |
| Height of the unit room | 300 mm |
| Number of the unit room | 5 |
| Diameter of a perforation of the perforated plate | 2 mm |
| Perforation rate | 8% |

Cultivation process:
Aeration was effected with air at the rate of 160 Nl/min. A main carbon source and nutrients as described above were supplied to the apparatus from the bottom at the rate of 15 l/hr.

COMPARATIVE EXAMPLE 1

For the comparison, a similar experiment to Example 1 was executed, excepting that the following apparatus was employed:

| Multistage fermentor; | |
|---|---|
| Diameter of the tower | 170 mm |

| -continued | |
|---|---|
| Height of the tower | 2,600 mm |
| Height of the unit room | 384 mm |
| Number of the unit room | 6 |
| Diameter of a perforation of the perforated plate | 2 mm |
| Perforation rate | 8% |

Results of Example 1 and Comparative Example 1

In both cases of Example 1 and Comparative Example 1, it was ascertained that operations arrived at steady state, thereafter samplings were carried out from each unit room for the measurement of the following items.

Figure 3:
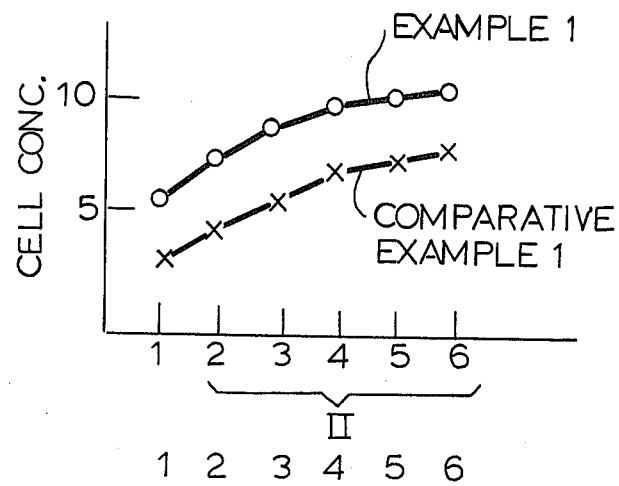
FIG. 3 is a curve showing comparison of cell concentrations between the present invention (Example 1) and Comparative Example 1.
Figure 4:
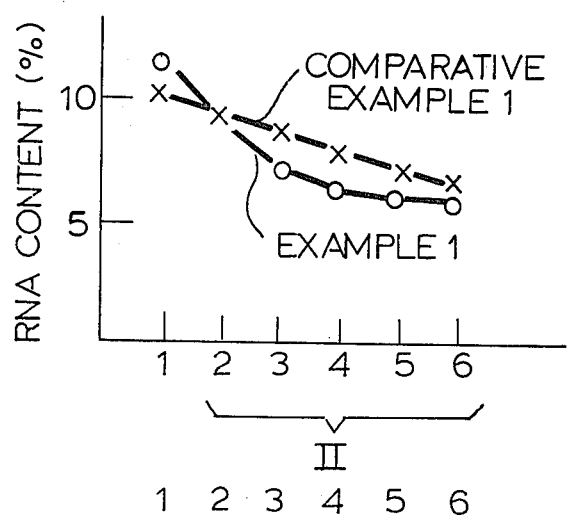
FIG. 4 is a curve showing comparison of RNA content between the present invention (Example 1) and Comparative Example 1.

The cell concentration of yeast was shown in FIG. 3 and RNA content was given in FIG. 4. The cell concentration was measured on dry weight wherein yeast was dried at 110° C. for 7 hours. The content of RNA was measured according to S.T.S. method.

It has now been understood from FIG. 3 that the present apparatus enables cultivation at a higher cell concentration than the apparatus used in Comparative Example 1. It has further been confirmed from FIG. 4 that the present apparatus permits the decrease of RNA content at an easy grade while the apparatus used in Comparative Example 1 lowers it straight, and that the degree of ripeness is enhanced by the apparatus of the present invention.

EXAMPLE 2

Yeast strain: *Candida lipolytica* IFO 0746
Main carbon sources and nutrients:

| n-paraffin | 2.5% (w/v) | $FeSO_4 \cdot 7H_2O$ | 200 ppm |
|---|---|---|---|
| $H_3PO_4$ | 4,000 ppm | $ZnSO_4 \cdot 7H_2O$ | 200 ppm |
| KCl | 4,000 ppm | $MnSO_4 \cdot 6H_2O$ | 20 ppm |
| $MgSO_4$ | 4,000 ppm | $CuSO_4 \cdot 5H_2O$ | 4 ppm |
| Ammonium sulphate | 500 ppm | Vitamine $B_1$ | 2 ppm |
| NaCl | 100 ppm | | |
| $CaCl_2$ | 200 ppm | | |

Cultivation conditions: Operation was effected continuously at 30° C., adjusting to pH 5.0 using a single fermentor.

Apparatus: The same as in Example 1.
Cultivation process: The same as in Example 1.

COMPARATIVE EXAMPLE 2

With the exception that the apparatus used in Comparative Example 1 was used, the experiment was conducted under the same conditions as in Example 2.

Results of Example 2 and Comparative Example 2

After ascertaining steady state, samplings were made to measure cell concentration. To compare productivities in cells, production amount per hour (kg/hr) was tabulated in Table 1.

TABLE 1

| | Production amount (kg/hr) | Yield* (%) |
|---|---|---|
| Example 2 | 394 | 105 |
| Comparative Example 2 | 300 | 80 |

*The yield was represented by percent of yeast cells dried per the amount of n-paraffin supplied.

What is claimed is:

1. An apparatus for cultivating microorganisms, comprising a cell multiplying means comprising
a cylindrical extended draft tube fermenter having a bottom and a top and a draft tube therein extending through part of said fermenter,
means for controlling the temperature of said fermenter,
inlet means disposed toward the bottom of said fermenter for supplying nutrients to said fermenter, and
means for supplying air to the bottom of said fermenter thereby to cause air to travel upward through said draft tube mixed with said nutrient; and
cell ripening means comprising
a plurality of cylindrical units connected to each other in vertical disposition with the bottommost unit connected to the top of said tube fermenter, and the topmost unit having an opening at the top thereof and having an outlet disposed toward the top thereof, each of said units comprising an inlet means disposed toward the bottom of each unit for supplying nutrients to each unit, each unit also having an opening at the bottom thereof and an opening at the top thereof, each unit having said top and bottom connected to another respective unit, each unit having perforated plates disposed across the bottom opening, and means for controlling the temperature of each unit, whereby the bottommost unit is connected to the top of said draft tube fermenter, and the topmost unit opening being to exhaust air, and the outlet being for removal of nutrient liquor, whereby nutrients supplied to the bottom of said draft tube fermenter through said inlet means of said fermenter is mixed in said draft tube with air supplied through said means for supplying air, and caused to rise until coming into approximate contact with the perforated plate of the bottommost unit of said cell ripening means and then caused to turn downward near the exterior periphery of said fermenter, and said air is caused to continue to rise toward the opening at the topmost unit, and wherein in each unit new nutrient is supplied through said inlet means and aerated by said air, thereby to cause increased cell concentration and improved cell ripening by enhanced oxygen transfer throughout said draft tube and throughout said units.

2. Apparatus of claim 1, wherein the ratio of the height of said draft tube fermenter to the diameter of the draft tube fermenter ranges from about 2 to about 10.

3. Apparatus of claim 1, wherein the ratio of the cross sectional area of the draft tube to that of the draft tube fermenter ranges from about 0.4 to about 0.9.

4. Apparatus of claim 1, wherein the draft tube is a double wall draft tube into which cooling water is introduced.

5. Apparatus of claim 1, wherein the perforated plate has numerous perforations of about 1 to about 10 mm in diameter and the ratio of the perforated area to the cross sectional area of the plate ranges from about 2 to about 20%.

6. A process for aerating microorganisms comprising the steps of carrying out cultivation of cells using an apparatus comprising
a cell multiplying means comprising
a cylindrical extended draft tube fermenter having a bottom and a top and a draft tube therein extending through part of said fermenter,
means for controlling the temperature of said fermenter,
inlet means disposed toward the bottom of said fermenter for supplying nutrients to said fermenter, and
means for supplying air to the bottom of said fermenter thereby to cause air to travel upward through said draft tube mixed with said nutrients; and
cell ripening means comprising
a plurality of cylindrical units connected to each other in vertical disposition with the bottommost unit connected to the top of said tube fermenter, and the topmost unit having an opening at the top thereof and having an outlet disposed toward the top thereof, each of said units comprising an inlet means disposed toward the bottom of each unit for supplying nutrients to each unit, each unit also having an opening at the bottom thereof and an opening at the top thereof, each unit having said top and bottom connected to another respective unit, each unit having perforated plates disposed across the bottom opening, and means for controlling the temperature of each unit, whereby the bottommost unit is connected to the top of said draft tube fermenter, and the topmost unit opening being to exhaust air, and the outlet being for removal of nutrient liquor, whereby nutrients supplied to the bottom of said draft tube fermenter through said inlet means of said fermenter is mixed in said draft tube with air supplied through said means for supplying air, and caused to rise until coming into approximate contact with the perforated plate of the bottomost unit of said cell ripening means and then caused to turn downward near the exterior periphery of said fermenter, and said air is caused to continue to rise toward the opening at the topmost unit, and wherein in each unit new nutrient is supplied through said inlet means and aerated by said air, thereby to cause increased cell concentration and improved cell ripening by enhanced oxygen transfer throughout said draft tube and throughout said units.

7. Process of claim 6, wherein batch cultivation is effected while recirculating the culture broth removed from the top of the multistage perforated plates fermenter to the draft tube fermenter.

8. Process of claim 7, wherein a main carbon source and nutrients are added to the culture broth removed, then aerated, thereafter recirculated to the draft tube fermenter.

9. Process of claim 6, wherein continuous cultivation is effected while removing the culture broth from the top of the multistage perforated plates fermenter.

10. Process of claim 6, wherein cultivation is effected while supplying a main carbon source and nutrients to the draft tube fermenter alone.

11. Process of claim 6, wherein cultivation is effected while supplying a main carbon source and nutrients to both multistage perforated plates fermenter and the draft tube fermenter.

* * * * *